United States Patent [19]

Knippscheer et al.

[11] Patent Number: 5,114,672
[45] Date of Patent: May 19, 1992

[54] METHOD FOR PRESERVING BLOOD FLUID

[75] Inventors: Hermann Knippscheer, Baldwin, N.Y.; Daniel D. Richard, Sedona, Ariz.

[73] Assignee: Cryo-Cell International, Inc., Baldwin, N.Y.

[21] Appl. No.: 573,646

[22] Filed: Aug. 27, 1990

[51] Int. Cl.⁵ .............................................. A01N 1/02
[52] U.S. Cl. .......................................... 122/41; 422/1; 422/40; 436/8; 436/18; 435/1; 435/2
[58] Field of Search ................. 422/1, 41, 44, 40; 436/8, 18; 604/4, 5, 6; 435/1, 2; 600/36; 623/1, 12

[56] References Cited

U.S. PATENT DOCUMENTS

| | | | |
|---|---|---|---|
| 3,894,530 | 7/1975 | Dardik et al. | 623/1 |
| 4,108,161 | 8/1978 | Samuels et al. | 600/36 |
| 4,240,794 | 12/1980 | Holman et al. | 8/94.33 |
| 4,627,419 | 12/1986 | Hills | 604/4 |
| 4,769,001 | 9/1988 | Prince | 604/4 |
| 4,804,363 | 2/1989 | Valeri | 422/41 |
| 4,919,823 | 4/1990 | Wisdom | 422/44 |

Primary Examiner—Robert J. Warden
Assistant Examiner—T. A. Trembley
Attorney, Agent, or Firm—R. Neil Sudol; Henry D. Coleman

[57] ABSTRACT

In a method for preserving umbilical cord blood, a severed umbilical cord is provided which has at least one tubular blood vessel closed at opposite ends to maintain fluid in the vessel. An anticoagulant is added to blood fluids in the vessel, and the blood fluid is moved in the vessel to distribute the anticoagulant throughout the blood. An associated apparatus comprises a container, a support within the container for supporting an umbilical cord, an injector or other fluid adding device engageable with the umbilical cord in the container for introducing an anticoagulant into at least one tubular vessel in the umbilical cord, and a fluid moving device at least partially inside the container for moving blood fluid contained in the tubular vessel.

20 Claims, 3 Drawing Sheets

METHOD FOR PRESERVING BLOOD FLUID

FIELD OF THE INVENTION

This invention relates to a method and apparatus for preserving blood fluid. More particularly, this invention relates to a method and apparatus for preserving or facilitating the preservation of blood from an umbilical cord. Even more particularly, this invention relates to a method and apparatus for preserving blood from a placenta and umbilical cord, while maintaining the blood at least temporarily in the umbilical cord.

BACKGROUND OF THE INVENTION

In many instances, the umbilical cord, like the placenta, is discarded after birth. However, it has been discovered that at least certain constituents of the umbilical cord may have a special usefulness. In a recent advance in the treatment of bone marrow defects in infants, physicians used the blood cells from the umbilical cord of an infant to aid in the regeneration of the stem cells in an older sibling. The blood was separated from the umbilical cord, subsequently frozen, and stored for seven months prior to infusion. Upon thawing, the cells were intravenously infused into the body of the recipient youngster. This technique provides several advantages over conventional marrow transplantation. Using the cord blood in this instance enabled transplant as soon as a compatible sibling was born, while candidates for marrow transplant generally must wait until the newborn is at least six months old. In addition, the procedure eliminates for the donor the pain of marrow extraction.

The use of umbilical cord blood for allogeneic and hematopoietic reconstitution in siblings has been since used in a number of cases. Clearly, umbilical cord blood represents a vase natural resource for medical, research and even identification purposes.

The amount of blood in the umbilical cord represents but a portion of the blood of an infant which is conventionally discarded at birth. The other portion of that disgarded blood resides in the placenta.

OBJECTS OF THE INVENTION

An object of the present invention is to provide a method and an associated apparatus for at least facilitating the preservation of blood from an umbilical cord.

Another object of the present invention is to provide such a method and apparatus which is fast and efficient.

Another, more particular, object of the present invention is to provide such a method and apparatus wherein sterility is maintained and contamination avoided.

A further particular object of the present invention is to provide such a method and apparatus wherein an anticoagulant is automatically mixed in with the blood from the umbilical cord.

SUMMARY OF THE INVENTION

A method for preserving blood fluid comprises, in accordance with the present invention, the steps of (a) providing a severed umbilical cord which has at least one tubular blood vessel closed at opposite ends to maintain fluid in the vessel, (b) adding an anticoagulant to blood fluid in the vessel, and (c) moving the blood fluid in the vessel to distribute the anticoagulant throughout the blood in the vessel.

Pursuant to a specific embodiment of the present invention, the step of moving includes the steps of connecting the vessel at opposite ends to a pump and operating the pump to circulate the blood in the vessel. Preferably, the step of adding is performed during at least a portion of the step of pumping. The step of adding may thus take the form of a gradual addition of the anticoagulant to the blood in the vessel. More particularly, the step of adding comprises the step of aspirating the anticoagulant into the blood of the vessel. Alternatively, the step of adding comprises the step of injecting the anticoagulant into the vessel.

Pursuant to an alternative specific embodiment of the present invention, the step of moving includes the step of vibrating or shaking the umbilical cord. In another alternative embodiment, the step of moving includes the step of squeezing the umbilical cord. Such squeezing may be implemented by rolling a roller along a portion of the umbilical cord.

In accordance with another feature of the present invention, the umbilical cord is placed into a transport and storage container and the umbilical cord is manipulated in the storage container to move the blood fluid in the vessel. Preferably, the step of manipulating includes the step of vibrating or shaking the umbilical cord or squeezing the umbilical cord, for example, with a roller member.

Pursuant to yet another feature of the present invention, the step of providing includes the steps of (a) providing a placenta with the umbilical cord connected thereto, (b) closing a free end of the umbilical cord, (c) manipulating the placenta to force blood therefrom into the umbilical cord, (d) closing an end of the umbilical cord opposite the free end, and (e) severing the umbilical cord from the placenta, while maintaining opposite ends of the umbilical cord closed. The opposite ends of the umbilical cord may be closed by clamping the cord.

An apparatus for at least temporarily preserving umbilical cord blood comprises, in accordance with the present invention, a container, a support within the container for supporting an umbilical cord, an injector or other fluid adding device engageable with the umbilical cord in the container for introducing an anticoagulant into at least one tubular vessel in the umbilical cord, and a fluid moving device at least partially inside the container for moving blood fluid contained in the tubular vessel.

Pursuant to a preferred embodiment of the present invention, the fluid moving device includes a pump, as well as coupling elements for connecting opposite ends of the umbilical cord blood vessel to the pump.

Pursuant to a further feature of the present invention, the fluid adding device includes an inlet connected to the pump at an inlet thereof.

Pursuant to an additional feature of the present invention, the fluid moving device includes means for vibrating the umbilical cord or for squeezing the umbilical cord.

DETAILED DESCRIPTION OF THE INVENTION

Figure 1:
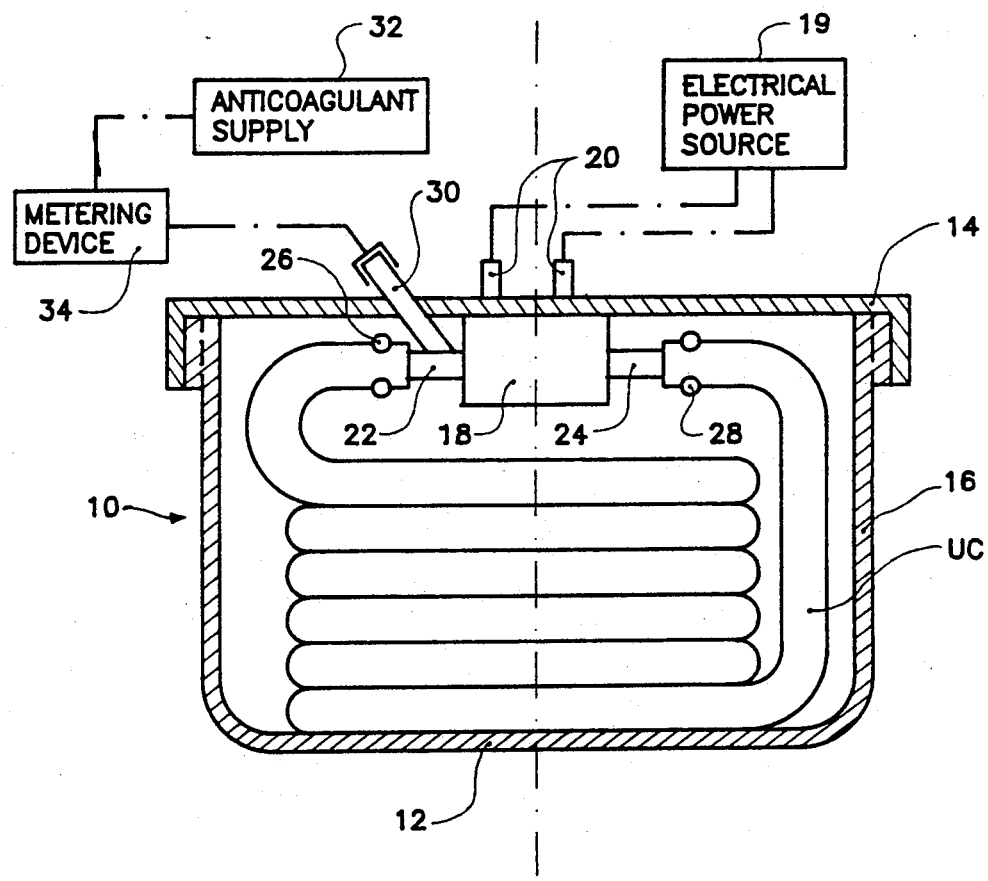
FIG. 1 is a cross-sectional view of an apparatus in accordance with the present invention for injecting or aspirating an anticoagulant into the vein of an umbilical cord and for circulating the anticoagulant and the cord blood to accelerate mixing thereof.

FIG. 1 shows an apparatus for injecting or aspirating an anticoagulant into the vein of an umbilical cord UC and for circulating the anticoagulant and the cord blood to accelerate mixing thereof, the apparatus comprising a container 10 with a bottom wall or panel 12 supporting umbilical cord UC. The apparatus serves to facilitate preservation of the cord blood or at least a substantial portion thereof which is contained in the vein of the umbilical cord.

Umbilical cord UC is severed from an infant and a placenta upon the afterbirth. In many cases, both ends of umbilical cord UC will have been temporarily clamped prior to insertion into the container of FIG. 1.

Container 10 includes a lid or cover 14 removably attachable to a container body 16 including bottom panel 12. Mounted to cover 14 on an inner surface thereof is a pump 18. Pump 18 is provided with a pair of electrical contacts 20 which extend through cover 14 for enabling coupling of pump 18 to a source of electrical power 19.

Pump 18 is further provided with an inlet tube 22 and an outlet tube 24 to which opposite ends of the umbilical cord vein (not separately illustrated) are connected. Expandable rings or clips 26 and 28 are provided for clamping the opposite ends of umbilical cord UC, and particularly the opposite ends of the vein thereof, to inlet tube 22 and outlet tube 24.

As further illustrated in FIG. 1, inlet tube 22 communicates with an auxiliary inlet tube 30 which is connected to a supply 32 of anticoagulant.

During operation of pump 18, anticoagulant is aspirated from supply 32 through inlet tubes 30 and 22. The rate of injection of the anticoagulant into the blood stream inside the umbilical cord vein may be controlled or regulated by a metering device or valve 34 disposed between supply 32 and pump inlet 22. Circulation of blood through the vein also results in a mixing of the anticoagulant and the blood fluids.

In an alternate method for preparing umbilical cord blood for storage and/or use, anticoagulant may be injected into the vein and/or arteries of an umbilical cord manually by means of a hypodermic needle. Preferably, such injection takes place after severing of the umbilical cord from the associated placenta.

Upon injection with anticoagulant, umbilical cord UC is manipulated, treated or otherwise processed to mix the injected anticoagulant an the blood fluids. As particularly illustrated in FIG. 2, umbilical cord UC may be placed on a support table 36 and covered with a sheet or web 38 of transparent polymeric material. The umbilical cord and web 38 are temporarily attached to table 36 via a plurality of clamps 40. Upon the securing of the cord UC to table 36, a motor 42 operatively coupled with the table is actuated to vibrate or shake the table to facilitate the mixing of the injected anticoagulant and the blood fluids.

Figure 3:
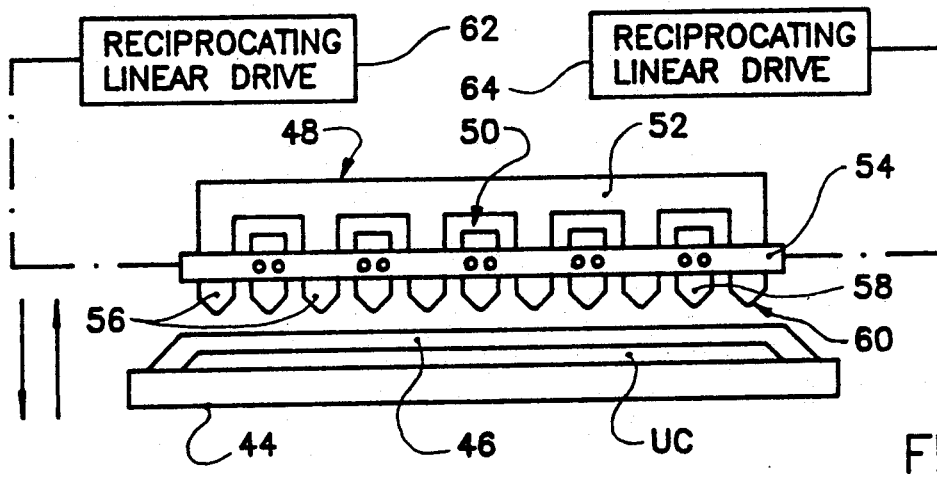
FIG. 3 is partially a block diagram and partially a schematic side elevational view of an apparatus for squeezing or pressing an umbilical cord at spaced locations therealong upon injection of an anticoagulant into the vein and/or artieries of the umbilical cord.

An alternative apparatus for accelerating the mixing of anticoagulant and cord blood in an umbilical cord UC is depicted in FIG. 3. A table 44 supports umbilical cord UC which is covered with a piece of plastic sheet material 46. The sheet material is exaggerated in thickness to facilitate its illustration in the drawing.

The apparatus shown in FIG. 3 operates to squeeze or press umbilical cord UC at spaced locations therealong and includes two vertically reciprocatable pressure members 48 and 50 each having at least one horizontally oriented carrier bar 52 and 54 and a plurality of vertically extending fingers 56 and 58. Each finger 56 and 58 is formed with a tapered, rounded tip 60. Bars 52 and 54 are reciprocated in a vertical direction by respective drives 62 and 64 with drive cycles which are 180° out of phase.

During operation of the apparatus of FIG. 3, fingers 56 contact sheet material 46 to press and squeeze umbilical cord UC simultaneously at a plurality of spaced locations. Bar 52 then moves upwardly, disengaging fingers 56 from sheet material 46 and umbilical cord UC, while bar 54 moves downwardly to place fingers 8 into contact with sheet material 46 and to thereby squeeze umbilical cord UC at a plurality of spaced positions laterally staggered with respect to the pressing positions of fingers 56. Fingers 56 and 58 rapidly alternate in their manipulation of umbilical cord UC and thereby cause a wave-like motion of the blood in the veins and arteries of the cord. This motion accelerates the mixing of the injected anticoagulant with the cord blood and enhances preservation of the blood.

Figure 4:
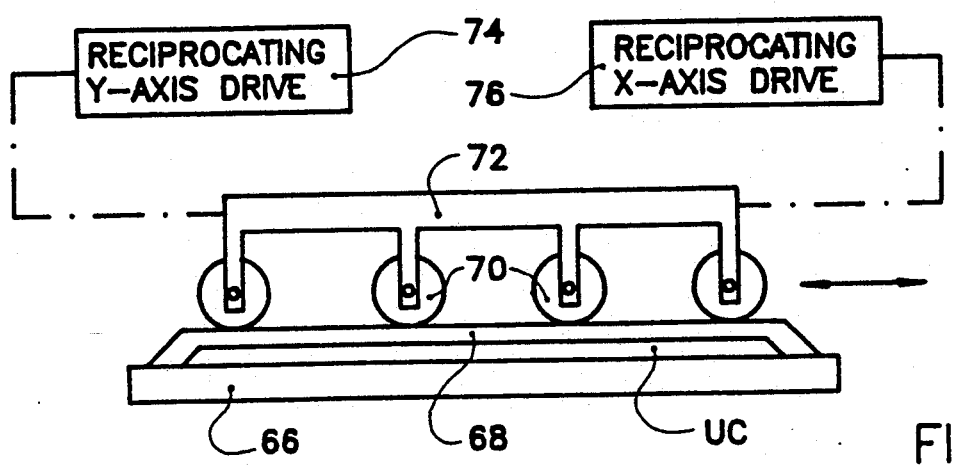
FIG. 4 is partially a block diagram and partially a schematic side elevational view of another apparatus for squeezing or pressing an umbilical cord at spaced locations therealong upon injection of an anticoagulant into the vein and/or artieries of the umbilical cord.

Yet another alternative apparatus for accelerating the mixing of anticoagulant and cord blood in an umbilical cord UC is illustrated in FIG. 4. Once again a table or platform 66 supports umbilical cord UC and a sterile plastic cover sheet 68. A plurality of rollers 70 are connected to a carriage 72 which in turn is operatively coupled with a first drive 74 for vertically shifting carriage 72 and rollers 70 alternately into and out of engagement with sheet 68. A second drive 76 is operatively linked to carriage 72 for rapidly reciprocating carriage 72 and rollers 70 in a horizontal direction upon engagement of the rollers with sheet 68. The resulting rolling of umbilical cord UC under a slight pressure causes the blood therein to move around and mix with injected anticoagulant. It is to be noted that rollers 70 may be lifted several times, and even laterally shifted, during a mixing process to facilitate diffusion of anticoagulant.

Figure 5:
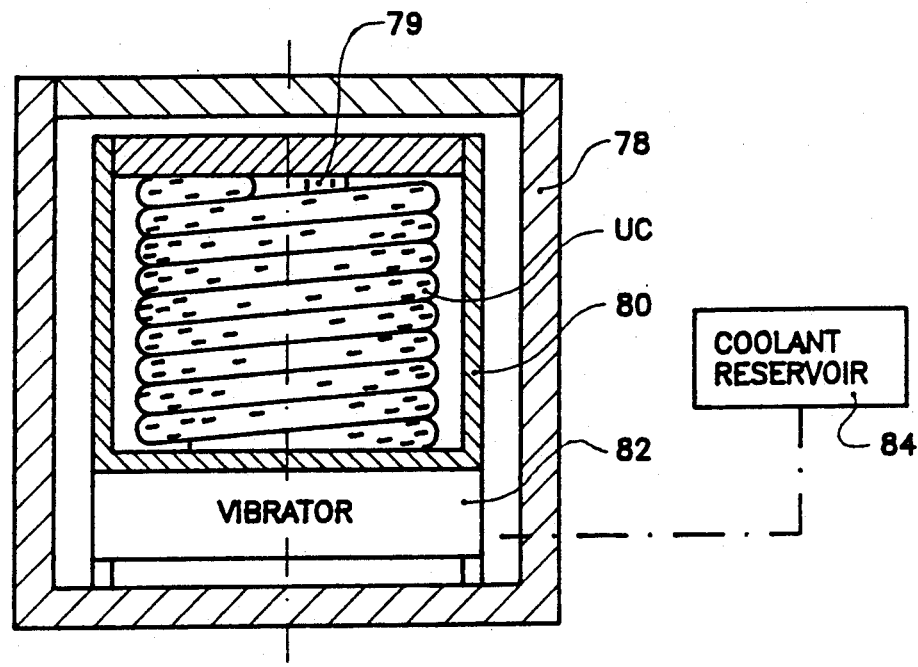
FIG. 5 is a schematic vertical cross-sectional view of a storage container with a device for vibrating or shaking a stored umbilical cord, in accordance with the present invention.

Upon addition of anticoagulant to blood in the vein and/or arteries of an umbilical cord UC, as described hereinabove, umbilical cord UC is placed in a container 78 (FIG. 5) for temporary storage prior to removal of the blood or prior to permanent storage of the umbilical cord UC and its conents for subsequent use thereof. As shown in FIG. 5, umbilical cord UC is wound about a cylinder 79 inside a cylindrical receptacle 80 which in turn is disposed on a vibrator component 82 inside container 78. Container 78 may also hold a coolant or other temperature controlling substance or be supplied with coolant from a reservoir 84. During storage and transport of umbilical cord UC in container 78, receptacle 80 and umbilical cord UC are subjected to continuous or periodic shaking by vibrator 82 to further mixing of anticoagulant and cord blood.

Figure 6:
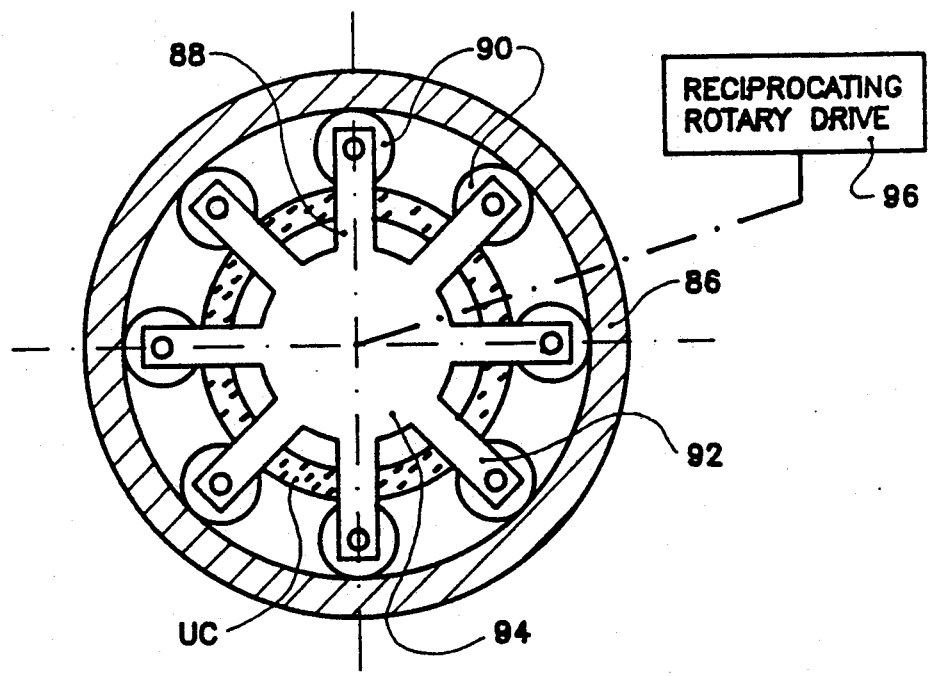
FIG. 6 is a schematic horizontal cross-sectional view of a storage container with a device for pressing or squeezing a stored umbilical cord, in accordance with the present invention.

Another storage container 86 is depicted in FIG. 6. Umbilical cord UC is wrapped around a centrally located cylinder 88 inside container 86. A plurality of rollers 90 are rotatably mounted at the outer ends of respective radially extending arms 92 circumferentially equispaced about the periphery of a driven member 94. Member 94 is shaken about a vertical axis by a reciprocating rotary drive 96. Rollers 90 are in contact with umbilical cord UC, perferably through a non-illustrated plastic sheet, and press umbilical cord slightly at angularly equispaced locations to further the mixing of anticoagulant and cord blood.

Figure 2:
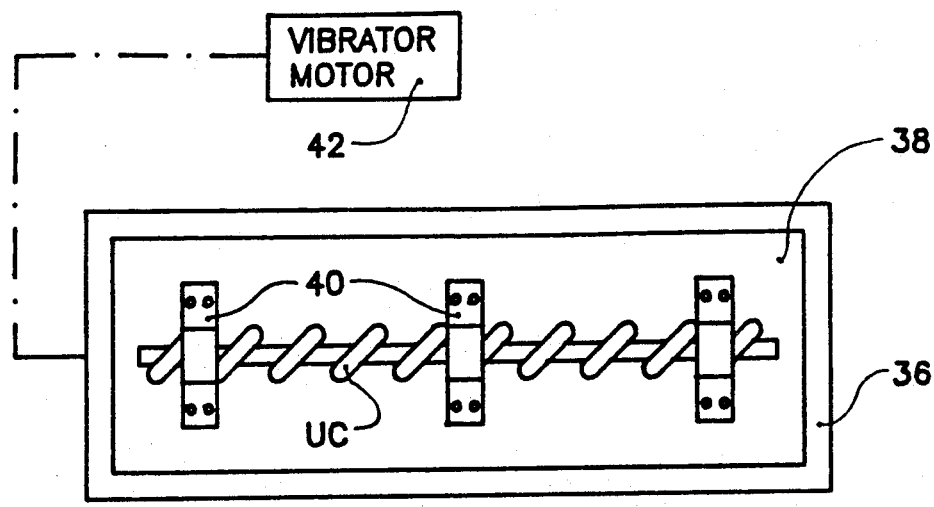
FIG. 2 is partially a block diagram and partially a top plan view of an apparatus for vibrating or shaking an umbilical cord upon injection of an anticoagulant into the vein and/or artieries thereof.

It is to be noted that the mixing process described hereinabove with reference to FIGS. 2–4 may be implemented instead with the instrumentation of FIGS. 5 and 6. Alternatively, the devices of FIGS. 5 and 6 may serve to supplement the action of the devices of FIGS. 2–4.

In another step in accordance with the present invention, the placenta (not shown) connected to umbilical cord UC is pressed or otherwise manipulated to squeeze infant blood therefrom into umbilical cord UC. The umbilical cord UC is then clamped at an end joined to the placenta and is severed therefrom. In this way the blood supply in the umbilical cord UC is augmented. The umbilical cord is then treated as described hereinabove.

It is to be noted that the deformation of the umbilical cord by fingers 56 and 58 or rollers 70 or 90 is not so great that a resulting pressure increase causes a rupture in the cord or at the clamps applied to the ends thereof.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A method for treating fluid including blood, comprising the steps of:
   providing an umbilical cord closed at opposite ends and containing a blood fluid to be treated;
   adding through said umbilical cord an additive to said blood fluid in said umbilical cord; and
   moving said blood fluid in said umbilical cord to distribute said additive throughout said blood fluid in said umbilical cord.

2. The method according to claim 1 wherein said step of moving includes the steps of opening said umbilical cord at said opposite ends and connecting said umbilical cord at said opposite ends to a pump and operating said pump to circulate said blood fluid in said umbilical cord.

3. The method according to claim 2 wherein said step of adding is performed during at least a portion of said step of pumping, said step of adding thus including a gradual addition of said additive to said blood fluid through said umbilical cord.

4. The method according to claim 3 wherein said step of adding comprises the step of aspirating said additive into said blood fluid of said umbilical cord.

5. The method according to claim 1 wherein said step of adding comprises the step of aspirating said additive into said blood fluid of said umbilical cord.

6. The method according to claim 1 wherein said step of adding comprises the step of injecting said additive into said blood fluid of said umbilical cord.

7. The method according to claim 1 wherein said step of moving includes the step of vibrating or shaking said umbilical cord.

8. The method according to claim 1 wherein said step of moving includes the step of squeezing said umbilical cord.

9. The method according to claim 1 wherein said step of moving includes the step of rolling a roller along a portion of said umbilical cord.

10. The method according to claim 1, further comprising the step of placing said umbilical cord into a transport and storage container; and
    manipulating said umbilical cord in said transport and storage container to move said blood fluid within said umbilical cord.

11. The method according to claim 10 wherein said step of manipulating includes the step of vibrating or shaking said umbilical cord.

12. The method according to claim 10 wherein said step of manipulating includes the step of squeezing said umbilical cord.

13. The method according to claim 10 wherein said step of manipulating includes the step of rolling a roller along said umbilical cord.

14. The method according to claim 10, further comprising the step of controlling the temperature in said transport and storage container.

15. The method according to claim 1 wherein said additive is an anticoagulant.

16. The method according to claim 15 wherein said step of providing includes the steps of providing a placenta with said umbilical cord connected thereto, closing a free end of said umbilical cord, manipulating said placenta to force blood therefrom into said umbilical cord, closing an end of said umbilical cord opposite said free end, and severing said umbilical cord from said placenta, while maintaining opposite ends of said umbilical cord closed.

17. A method for treating fluid including blood, comprising the steps of:
    providing an umbilical cord closed at opposite ends and containing a blood fluid to be treated; and
    at least partially automatically moving said fluid in said umbilical cord to prevent coagulation of blood in said fluid.

18. The method according to claim 17 wherein said step of moving includes the step of at least partially automatically vibrating or shaking said umbilical cord.

19. The method according to claim 17 wherein said step of moving includes the step of at least partially automatically squeezing said umbilical cord.

20. The method according to claim 17 wherein said step of moving includes the step of at least partially automatically rolling a roller along a portion of said umbilical cord.

* * * * *